United States Patent [19]

Bullara

[11] Patent Number: 4,573,481
[45] Date of Patent: Mar. 4, 1986

[54] IMPLANTABLE ELECTRODE ARRAY

[75] Inventor: Leo A. Bullara, Glendora, Calif.

[73] Assignee: Huntington Institute of Applied Research, Pasadena, Calif.

[21] Appl. No.: 623,981

[22] Filed: Jun. 25, 1984

[51] Int. Cl.$^4$ .............................................. A61N 1/04
[52] U.S. Cl. ................................................ 128/784
[58] Field of Search .......... 128/784, 785, 642, 419 E, 128/419 P, 381

[56] References Cited

U.S. PATENT DOCUMENTS

| | | | |
|---|---|---|---|
| 415,274 | 11/1889 | Kang | 128/381 |
| 3,578,344 | 3/1971 | Bolduc | 128/419 P |
| 3,760,812 | 9/1973 | Timm et al. | 128/419 E |
| 4,011,861 | 3/1977 | Enger | 128/419 E |
| 4,026,300 | 5/1977 | DeLuca et al. | 128/785 |
| 4,026,303 | 5/1977 | Babotoi | 128/785 |
| 4,198,991 | 4/1980 | Harris | 128/784 |

Primary Examiner—William E. Kamm
Attorney, Agent, or Firm—Christie, Parker & Hale

[57] ABSTRACT

An implantable helical electrode assembly configured to fit around a nerve for electrically triggering or measuring an action potential or for blocking conduction in nerve tissue. A multiconductor flexible cable connects the electrode to an implanted signal receiver, and the assembly may include multiple individual flexible ribbon electrodes each partially embedded in a portion of the peripheral surface of a helically formed dielectric support matrix. The spiral configuration of the assembly is easy to install around a nerve bundle during surgical implantation, and the resiliency of the assembly minimizes the risk of damage to nerve tissue. The tissue-contacting surface of each electrode is roughened to increase the electrode surface area.

19 Claims, 12 Drawing Figures

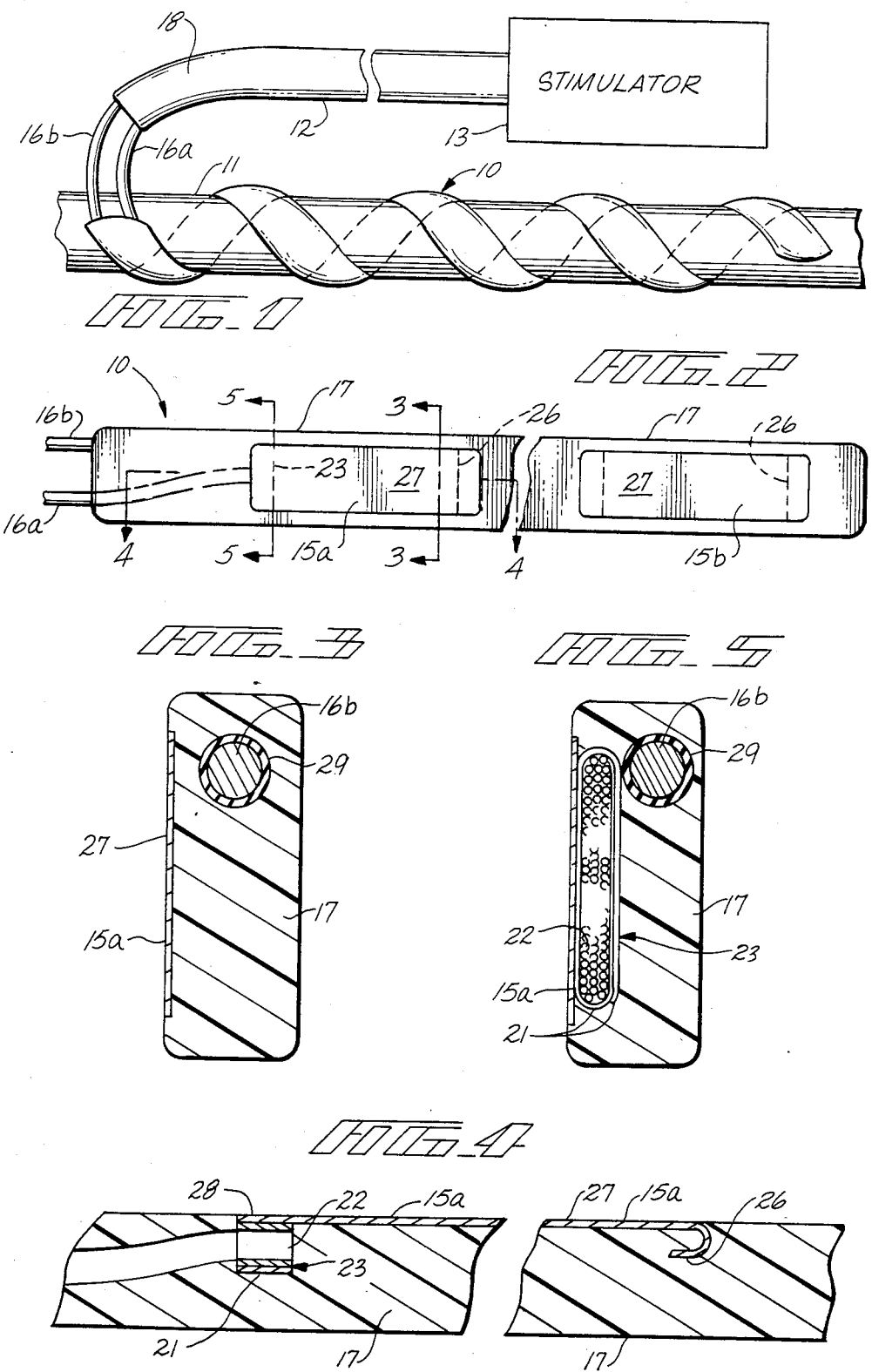

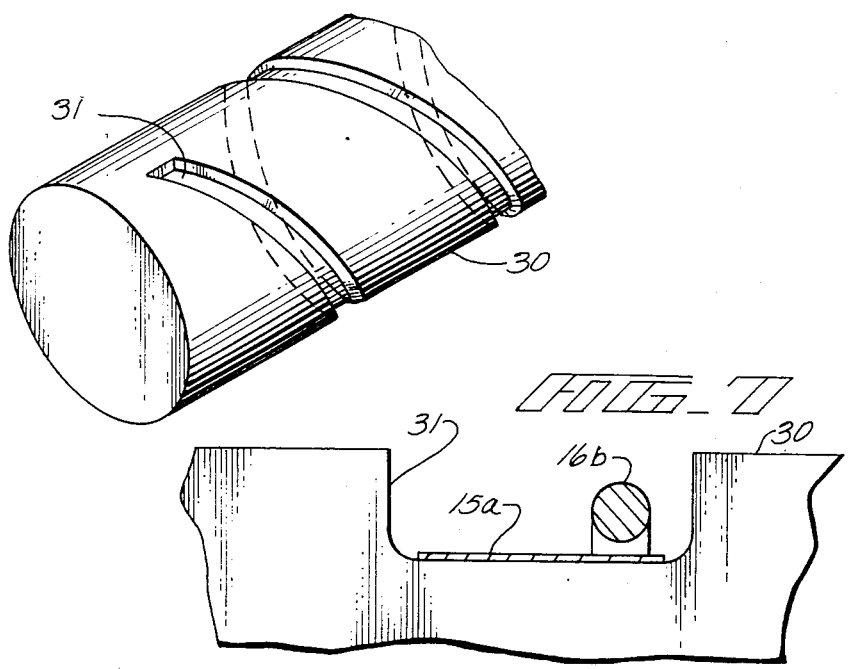
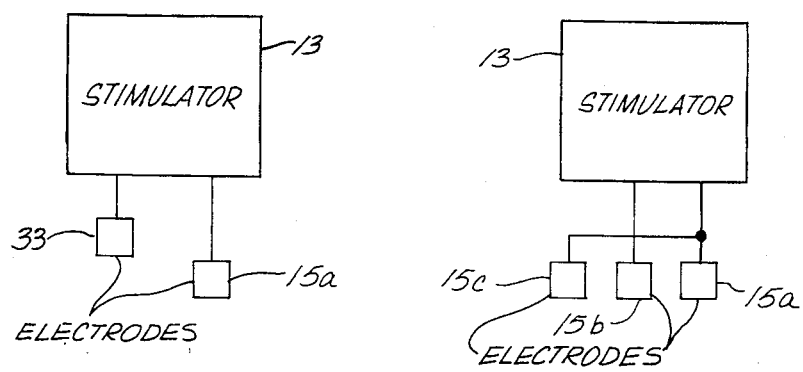

IMPLANTABLE ELECTRODE ARRAY

BACKGROUND OF THE INVENTION

It has been known for almost 200 years that muscle contraction can be controlled by applying an electrical stimulus to the associated nerves. Practical long-term application of this knowledge, however, was not possible until the relatively recent development of totally implantable miniature electronic circuits which avoid the risk of infection at the sites of percutaneous connecting wires. A well-known example of this modern technology is the artificial cardiac pacemaker which has been successfully implanted in many patients.

Modern circuitry enables wireless control of implanted devices by wireless telemetry communication between external and internal circuits. That is, external controls can be used to command implanted nerve stimulators to regain muscle control in injured limbs, to control bladder and sphincter function, to alleviate pain and hypertension, and to restore proper function to many other portions of an impaired or injured nerve-muscle system.

To provide an electrical connection to the peripheral nerve which controls the muscles of interest, an electrode (and sometimes an array of multiple electrodes) is secured to and around the nerve bundle. A wire or cable from the electrode is in turn connected to the implanted package of circuitry. The present invention is directed to an improvement in this type of electrode.

A widely used prior-art electrode assembly is formed from a tube of silicone rubber with one or more electrodes secured on the inner surface of the tube. An end-to-end slit is cut through the tube sidewall so the tube can be opened and fitted over the nerve bundle. When so installed, the resiliency of the tube causes it to surround the nerve bundle to urge the electrode against the surface of the tissue, and the tube may also be provided with suture flaps for additional anchorage. Due to its construction, this style of assembly is usually called a "cuff" electrode.

Animal-implant studies suggest that cuff electrodes can cause neural damage, and are not wholly satisfactory for long-term implantation. The probable causes of these problems can be summarized as follows:

A. Although having some radial flexibility to enable installation over the nerve, the silicone-rubber tube or sleeve is relatively stiff to insure that the restoring force of the resilient material will position the electrode against the nerve surface to insure adequate electrical contact. Excessive gripping and compression of the nerve by the cuff can cause nerve damage by decreasing blood and axoplasmic flow, and by constricting nerve fibers with resulting loss of function. This problem is accentuated by temporary swelling of the nerve caused by the trauma of surgical implantation of the electrode.

B. If a cuff electrode is loosely fitted to limit pressure atrophy of the nerve, a poor electrical contact is made, and this contact is further degraded in time by ingrowth of connective tissue between the cuff and nerve. This ingrowth is sometimes sufficiently marked to lead to compression damage to the nerve as discussed above, or it may cause complete separation of the cuff and nerve.

C. The nerve is encased within the full length of the cuff, blocking a normal metabolic exchange between the nerve and surrounding tissue. That is, a normal and desired fluid interchange between the nerve and its surrounding environment is prevented or sharply decreased over the length of the cuff.

D. In addition to compression damage, mechanical trauma to the nerve can be caused by torque or bending forces applied by the cuff and its relatively stiff cable during muscle and body movement. These forces may even displace the nerve bundle out of the cuff.

E. Conventional cuff assemblies use electrodes of small surface area, and the resulting high density of electrical charge at the electrode-nerve interface can result in an undesired electrochemical deposition of electrode material on the nerve sheath.

The helical electrode of this invention overcomes or minimizes the problems which have been observed with implanted cuff electrodes. Broadly, the new electrode assembly includes a spiral or helical array configured to fit around a nerve bundle, and having at least one plate, foil, or wire electrode on its surface. A flexible cable connects the helical array to an implanted biostimulator electronics package.

During surgical implantation, the softness and pliability of the spiral array enables it to be gently wound around the nerve with minimal nerve manipulation and constriction of blood vessels. Any post-operative edema or swelling of the nerve is accommodated by a gentle yielding and radial expansion of the spiral which minimizes the risk of compression atrophy of the nerve tissue. The open construction of the helix significantly reduces coverage of the nerve periphery to promote a more normal fluid exchange with surrounding tissue. A good electrical contact between electrode and nerve is maintained, and the problem of growth of connective tissue into the electrode-nerve interface is minimized.

In further contrast to cuff electrodes, the spiral array completely encircles the nerve to insure contact with sub-bundles within the main nerve bundle. The resiliency of the array and connecting cable provide good isolation of the nerve from mechanical loads during body and muscle movement. Importantly, the effective surface area of each electrode is made larger than its plane geometric area by a peening or other roughening operation to reduce electrical charge density at the nerve-electrode interface.

SUMMARY OF THE INVENTION

Briefly stated, the invention comprises an electrode assembly for surgical implantation on a peripheral nerve, the assembly including a helically formed supporting matrix. A conductive electrode (preferably made of activated iridium) is secured to an inner, side, or exterior surface of the helical matrix, and a connection means is secured to the electrode and extends from the matrix. Preferably, the electrode is partially embedded in the matrix so only a bare electrode surface facing the axis of the helical matrix is exposed.

In a preferred form the surface of the exposed electrode face is roughened to increase the effective area of the electrode surface. The number of individual electrodes in the assembly is dictated by the specific form of neurostimulation to be achieved, but the assembly is useful with either single or plural electrodes.

BRIEF DESCRIPTION OF THE DRAWINGS

FIG. 1 is a view of an electrode assembly according to the invention as mounted on a peripheral nerve and coupled to an implanted neurostimulator circuit (shown in phantom line);

FIG. 2 is a plan view of the electrode assembly when unwound from the helical form into a flat strip;

FIG. 3 is a sectional view on line 3—3 of FIG. 2;

FIG. 4 is a sectional view on line 4—4 of FIG. 2;

FIG. 5 is a sectional view on line 5—5 of FIG. 2;

FIG. 6 is a view of a mandrel;

FIG. 7 is a view of a portion of the electrode assembly wound on the mandrel;

FIG. 8 is a schematic diagram of a single-electrode system;

FIG. 9 is a schematic diagram of a triple-electrode system;

DESCRIPTION OF THE PREFERRED EMBODIMENT

Figure 10:
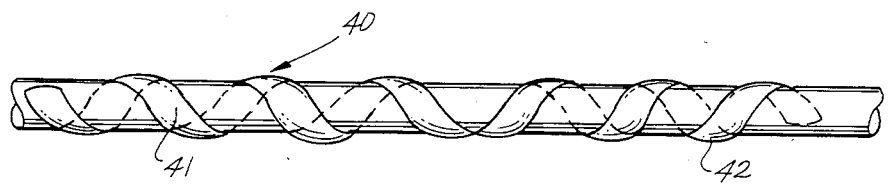
FIG. 10 is a view of an alternative electrode assembly having oppositely wound spiral segments.

FIG. 1 shows an helical electrode assembly 10 according to the invention, and installed on a peripheral nerve 11. A cable 12 connects assembly 10 to an implantable neurostimulator or bioelectronic receiver 13 arranged to receive command signals transmitted from outside the body. The receiver sends current signals to the electrode assembly and the nerve in response to the command signals. Bioelectronic receivers of various styles are known in the art, and, for brevity, will not be discussed in detail.

Referring to FIGS. 2-4 the assembly (shown as "unwound" into an elongated flat strip) includes one or more electrodes 15, a connecting wire 16 secured to each electrode, and a strip-like supporting matrix 17 which holds and positions the wires and electrodes. Depending on the physiological function to be accomplished, the assembly may have one, two, three, or more electrodes. The configuration shown in the drawings has two electrodes 15a and 15b, and the associated wires are designated as 16a and 16b.

Long-term implantation is desired in many applications of the electrode assembly, and it is important that the assembly components be capable of sterilization and made of materials which are acceptable to the body. Preferably, the electrodes are made of activated iridium, but platinum or rhodium (or alloys of these metals) are alternative materials. The supporting matrix is a moldable medical-grade silicone such as sold under the trademark Dow-Corning 905 (Adhesive Type A), or alternating layers of this material and Dow-Corning 382 medical-grade silicone. The latter material enables better control of matrix resiliency, and it bonds well to the Dow-Corning 905 material.

The use of activated pure iridium in neural-stimulation electrodes is described in detail in a paper of Robblee, Lefko and Brummer published in 130 Journal of the Electrochemical Society 731-33 (1983). The iridium ribbon material is typically activated by formation of a high-valence iridium-oxide surface layer on the ribbon. Charge injection is facilitated by oxidation and reduction of this surface layer, and undesired erosion of the underlying pure metal is reduced or eliminated.

Connecting wires 16 are preferably highly flexible stranded conductors, and a wire formed of about 45 strands of very fine (0.0005 to 0.0006 inch diameter) stainless-steel wire is satisfactory. Between the electrode assembly and the bioelectronic receiver, each wire has an insulating jacket 18 (FIG. 1) of a medical-grade silicone as mentioned above.

In making prototype models of the assembly, an initial step is to strip the insulating jacket from the end of each wire 16, and then to wrap the bare wire spirally or helically around a small-diameter (e.g., in the range of about 2 to 5 millimeters, depending on the size of the nerve for which the assembly is intended) cylindrical mandrel (not shown). The wire and mandrel are then heated in a vacuum furnace to about 800° C. to anneal and stress relieve the strands, and to give the wire a permanent spiral configuration. This step is completed under high vacuum to avoid oxidation which can reduce strand strength and interfere with subsequent electrode welding.

With the exposed end of the wire now set in a corkscrew shape, a narrow (about 0.25-0.4 mm) activated-iridium ribbon 21 is wrapped around tip 22 of the wire end for about one and one-half turns as shown in FIGS. 4 and 5. The ribbon is resistance welded to the wire tip with a parallel-electrode welder which flattens the ribbon and stranded wire into a pad or tab 23 which can be readily welded to the associated electrode 15.

Each electrode 15 is initially formed as a generally rectangular strip of activated-iridium ribbon of about 0.0005-inch thickness. In a typical configuration, the ribbon is about 0.75 to 1.0 mm wide, and of sufficient length to spiral entirely around the diameter of the selected nerve.

For example, if the nerve on which the electrode assembly is to be implanted is about 2 mm in diameter, and the helical pitch of the electrode is about 3 mm, the electrode length should be at least 7 mm (and preferably 8 or 9 mm as a safety factor). This insures that the installed electrode wire surrounds the nerve to deliver stimulus signals to the sub-bundles which comprise the main nerve bundle.

As shown in FIG. 4, one end 26 (remote from the end to be welded to tab 23) of the electrode ribbon is folded back on itself, the direction of the fold being away from a front surface 27 which will face and contact the nerve when the assembly is implanted. An opposite end 28 of the ribbon is then positioned over tab 23 of associated connecting wire 16, and the ribbon and tab are resistance welded together.

An important step in completing preparation of the electrode is to increase the surface roughness of front surface 27. While the surface roughening can be done in a number of ways, a simple and effective technique is to peen or "sandblast" surface 27 with very small glass beads, or preferably with salt crystals which can be easily dissolved and removed to insure electrode cleanliness after the desired degree of roughness is achieved.

The purpose of surface roughening is to increase significantly the effective surface area of the electrode, and ultimately to enable biostimulation of a nerve bundle at a relatively low charge density at the nerve surface. Surface roughening can easily increase the effective surface area by a factor of 20, and surface-area increases in the range of 40 to 50 are believed feasible.

The coiled end of wire 16 and the now-secured electrode are next dipped in a bath (preferably agitated by ultrasonic energy) of a liquid epoxy such as sold under the trademark Epoxylite. When the exposed metal surfaces have been fully coated with liquid epoxy, the wire and electrode are removed from the bath, and all epoxy is removed from front surfce 27 which will contact the nerve when the electrode is installed.

The wire and electrode ribbon are then baked to cure the epoxy, and to form a flexible layer of insulating material 29 on the wire and the back surface of the electrode. The specified epoxy material is presently preferred as it bonds well to silicone in the subsequent manufacturing steps described below.

An arbor or mandrel 30 as shown in FIG. 6 is used in completing the electrode assembly. The mandrel has a helical groove 31 formed in its surface, and the groove has a generally rectangular cross section. The groove is typically about 0.030 to 0.040 inch deep, and is slightly wider than the electrode ribbon being used. The helical pitch of the groove corresponds to the pitch desired in the finished spiral electrode, and the inside diameter of the groove corresponds to the desired inside diameter of the finished electrode.

Wires 16a and 16b, and associated electrodes 15a and 15b are now wound into groove 31 as shown in FIG. 7. Wire 16b is longer than wire 16a so the electrodes will be axially spaced apart, preferably by at least about ten millimeters. Silicone of the type already described is then deposited in the groove to encapsulate the wires, and to surround the electrodes with the exception of front surfaces 27 which remain exposed. The silicone extends away from the electrodes sufficiently far to join and become bonded to insulating jacket 18 on each wire.

Preferably the mandrel groove is slightly overfilled to provide a softly rounded top surface on the resulting assembly. As shown in FIGS. 2 and 4, the silicone flows into folded end 26 of each electrode to increase the physical bond between resulting supporting matrix 17 and the electrode. The extra width of the mandrel groove enables the matrix to overhang the thin edges of the electrodes to prevent abrasion or cutting of the nerve bundle.

When the silicone matrix has cured, the completed assembly is stripped away from the mandrel, and is ready for use. Surgical implantation is conventional, and the electrode is gently wrapped around the exposed nerve. The wrapping operation starts at the cable end of the matrix and proceeds toward the opposite free end of the matrix.

When so installed, the open construction of the helical electrode minimizes interruption of the necessary fluid exchange between the nerve and its surrounding environment. Swelling or edema of the nerve as a result of surgical manipulation is accommodated by a slight "unwinding" of the helical coil to enlarge the coil diameter in response to tissue pressure. Good electrical contact of the electrode and nerve is provided by the gentle springiness of the silicone matrix, and tests have shown that interruptive ingrowth of fatty or connective tissue is significantly reduced as compared to that encountered with cuff-type electrodes.

The helical electrode assembly is useful in a variety of ways in association with the peripheral nerve system, and the number and spacing of electrodes (and the dimensions of the helix) will vary depending on the objective to be achieved. In some cases, a single electrode only is needed, and this arrangement is shown in schematic form in FIG. 8, with the second contact being made by a common or "indifferent" electrode 33 which may be remote from the nerve.

FIG. 9 shows the wiring arrangement of one form of a three-electrode array which is useful in certain muscle-stimulation applications. Voltage and current levels can vary considerably, but a typical stimulating pulse is in the range of 15 volts at about 3 milliamperes. As mentioned above, the range of application of the electrode assembly is not limited to muscle stimulation, and blocking of nerve conduction or monitoring of action potentials are other suitable uses.

Depending on the cross-sectional shape of the nerve to be stimulated, it may be desirable to form the electrode with a generally elliptical (in cross section) central opening to provide good conformance with the nerve surface. Variations of this type are easily achieved by changing the cross-sectional shape of mandrel 30.

Another alternative arrangement is to form an electrode assembly 40 (FIG. 10) having oppositely wound spiral segments 41 and 42. The oppositely wrapped segments are believed to be useful in minimizing contraction or migration of the electrode assembly in situations where the associated nerve bundle is subject to active skeletal or muscle movement.

A further alternative electrode configuration is shown in FIGS. 11 and 12, and it again uses a pair of spaced-apart electrodes 51 and 52 which are preferably made of activated iridium. To provide improved adhesion to subsequently applied insulating materials and the silicone matrix, dimples or small holes 53 are preferably formed along the periphery of each generally rectangular electrode.

Figure 11:
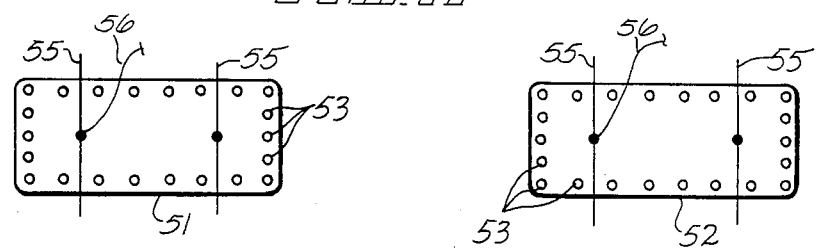
FIG. 11 is a plan view of a pair of electrodes for another embodiment of the invention.

As shown in FIG. 11, a pair of short spaced-apart tie wires 55 and a long connecting wire 56 are spot welded to the back surface of each electrode. Both the tie wires and connecting wires can be 0.002-inch diameter platinum/10% iridium wire. The wires and back surface of the electrode are then coated with Epoxylite material which is baked at about 170° C. The front surfaces of the electrodes which will contact the nerve bundle are of course left uncoated.

Figure 12:
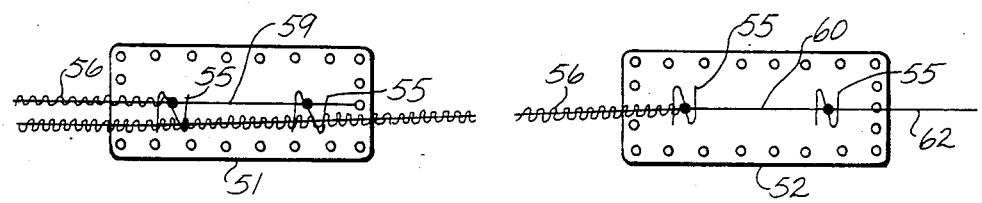
FIG. 12 is a view similar to FIG. 11 after connecting wires to the electrodes have been completed.
Figure 13:
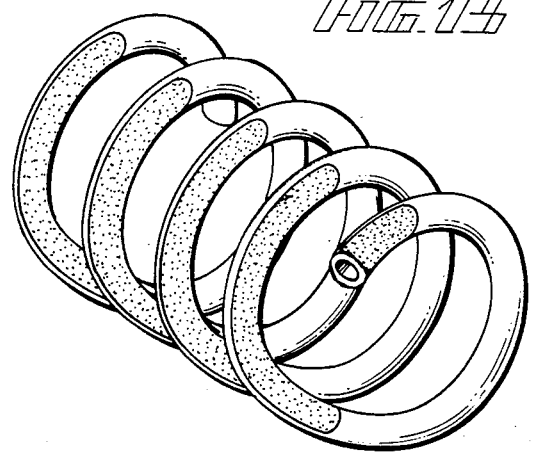

A thread 59 of 5-0 dacron suture material is then placed on the back of electrode 51, and a longer second thread 60 of the same material is positioned across the rear surfaces of both electrodes 51 and 52. Tie wires 55 are folded over the threads to secure them in place as shown in FIG. 12. Connecting wires 56 are then spiral-wound along the threads to provide a strain-relieved pair of connections to the respective electrodes. A light coating of silicone Type A adhesive is then applied to the spiral-wound wires, and allowed to dry.

Thread 59 terminates within the perimeter of electrode 51, but thread 60 extends beyond electrode 52 by several centimeters as shown in FIG. 12. This tag end 62 of thread 60 provides a "tail" which can be gripped by the surgeon to gently wind the spiral electrode around a nerve bundle.

The remaining fabrication steps are the same as already described with respect to assembly 10. That is, the electrodes and connecting wires are wrapped around a spiral mandrel, and covered with a supporting matrix of silicone material to form the complete spiral electrode assembly. Connecting wires 56 extend from the completed spiral assembly for connection to wires in a connecting cable (not shown).

In some applications of the spiral electrode assembly of this invention on the peripheral nervous system (in, for example, the arms or legs), the nerve may be adjacent a major muscle or other body structure which presses the electrodes against the nerve with considerable pressure in certain body positions. In other body positions, this pressure is released, perhaps leaving a small fluid-filled space between the electrode and nerve surface. These electrode-nerve spacing variations can sometimes present a problem in that the stimulation effectiveness of a given electrical signal is significantly influenced by spacing.

In such applications, it is unnecessary that the electrodes be located on the inside diameter of the supporting spiral matrix, and the electrodes are instead positioned on the side surfaces (or even the top surface) of the spiral matrix. Such side- or top-mounted electrodes should extend entirely around the nerve for the reasons described above, and the electrodes are preferably again formed of activated iridium foil or wire. This arrangement sometimes requires a somewhat higher level stimulating signal, but small spacing variations due to muscle or skeletal movement have little effect due to the larger average separation of the electrode and nerve surface.

When a side- or top-mounted electrode array is used, the electrode assembly is preferably covered with a loose-fitting insulating sheath or cuff to minimize outwardly directed charge injection away from the nerve into overlying tissue. The insulating sheath tends to confine charge injection to the target nerve, and reduces unwanted stimulation of adjacent tissue.

The manufacturing techniques described above are useful for small-scale production, but the assembly is suitable for injection-molding manufacturing methods at a substantial reduction in cost. The assembly is useful in a variety of implantable applications, and is believed to be a significant improvement over existing nerve electrodes.

What is claimed is:

1. An electrode assembly for surgical implantation on a nerve of the peripheral nerve system, comprising:
   a flexible helically formed supporting matrix of dielectric material;
   a flexible conductive electrode secured to the surface of the matrix, the electrode having front and rear surfaces and side edges, the front surface being exposed and not covered by the matrix, the electrode occupying only a portion of the cross-sectional periphery of the matrix; and
   flexible connection means connected to the electrode and extending from the matrix;
   the matrix and electrode generally forming a multi-turn hollow helix wibh a free end and without a supporting core, the turns being resiliently movable with respect to each other to enable the helix to be wrapped around an unsevered nerve, the helix having a central passage therethrough of size and configuration generally conforming to the external size and configuration of the nerve.

2. The assembly defined in claim 1 wherein the electrode is partially embedded in the matrix.

3. The assembly defined in claim 2 wherein the matrix extends over the rear surface and side edges of the electrode.

4. The assembly defined in claim 2 wherein one end of the electrode is folded rearwardly and the folded end is fully embedded in the matrix.

5. The assembly defined in claim 2 wherein the connection means is embedded in the matrix between the electrode and an end of the matrix.

6. The assembly defined in claim 1 wherein the front surface of the electrode is roughened to increase the effective area of the surface.

7. The assembly defined in claim 6 wherein the degree of surface roughening increases the effective surface area by a factor of at least 20 as compared to a perfectly smooth surface.

8. The assembly defined in claim 1 wherein the connection means includes a flexible stranded wire.

9. The assembly defined in claim 8 wherein the connection means further includes a conductive ribbon wrapped around an end of the wire and welded thereto to form a flattened connection tab for attachment to the electrode.

10. The assembly defined in claim 1 wherein the matrix is molded silicone, the electrode is partially embedded in the matrix with only the electrode front surface exposed, the front surface being roughened to increase its effective area by a factor of at least 20 as compared to a perfectly smooth surface, and the connection means includes a flexible stranded wire embedded in the matrix between the electrode and an end of the matrix.

11. The assembly defined in claim 1 wherein the electrode is made of a ribbon of activated iridium, and the electrode is secured to the inner surface of the matrix to face the central axis of the matrix helix.

12. An electrode assembly for surgical implantation around a nerve, comprising:
    a flexible supporting matrix formed substantially in the shape of a spiral helix;
    a plurality of spaced-apart flexible conductive ribbon electrodes secured to and arrayed along an inner surface of the matrix, each electrode occupying only a portion of the cross-sectional periphery of the matrix and having a separate flexible conductor extending therefrom; and
    the conductors being embedded in the matrix to extend from the respective electrodes to an end of the matrix;
    the matrix and electrodes generally forming a multi-turn hollow helix with a free end and without a supporting core, the turns being resiliently movable with respect to each other to enable the helix to be wrapped around an unsevered nerve, the helix having a central passage therethrough of size and configuration generally conforming to the external size and configuration of the nerve.

13. The assembly defined in claim 12, wherein the ribbon electrodes are partially embedded in the inner matrix surface with each electrode having an exposed nonembedded front surface facing a central axis of the helix, and wherein the conductors external to the matrix form a flexible connecting cable.

14. The assembly defined in claim 13 wherein the front surfaces of the electrodes are roughened to provide an increased effective surface area.

15. The assembly defined in claim 14 wherein the effective surface area is increased by a factor of at least 20 as compared to a perfectly smooth surface.

16. The assembly defined in claim 15 and further comprising an implantable biomedical electronic signal device connected to the cable of the assembly.

17. The assembly defined in claim 13, wherein the electrodes are made of ribbons of activated iridium.

18. The assembly defined in claim 1 wherein the electrode extends along at least one full turn of the matrix to enable surrounding of the nerve by the electrode, and wherein the matrix is impervious to body fluids.

19. The assembly defined in claim 13 wherein at least one of the electrodes extends along at least one full turn of the matrix to enable surrounding of the nerve by said one electrode, and wherein the matrix is impervious to body fluids.

* * * * *